Figure 1:
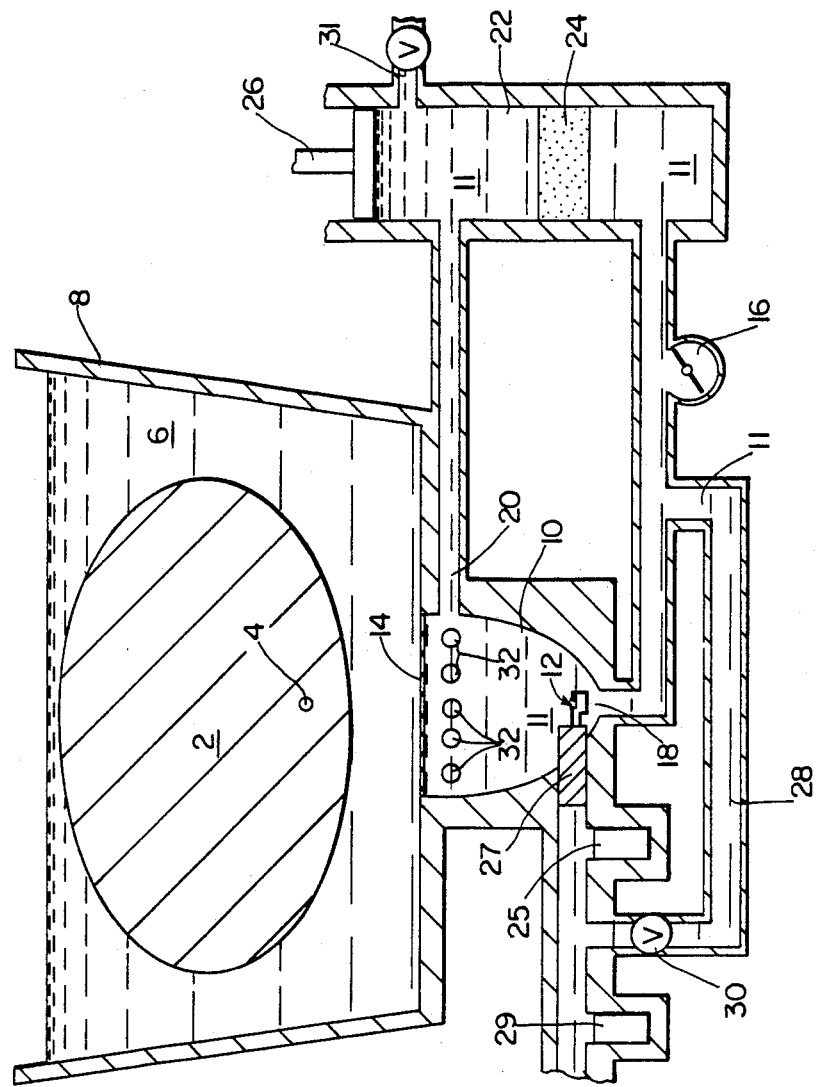

United States Patent [19]
>
> Forssmann et al.
>
> [11] Patent Number: 4,530,358
>
> [45] Date of Patent: Jul. 23, 1985

[54] APPARATUS FOR COMMINUTING CONCRETIONS IN BODIES OF LIVING BEINGS

[75] Inventors: Bernd Forssmann, Friedrichshafen; Othmar Wess, Immenstaad; Hendrik Zech, Überlingen; Christian Chaussy, Germering, all of Fed. Rep. of Germany

[73] Assignee: Dornier System GmbH, Friedrichshafen, Fed. Rep. of Germany

[21] Appl. No.: 471,673

[22] Filed: Mar. 3, 1983

[30] Foreign Application Priority Data

Mar. 25, 1982 [DE] Fed. Rep. of Germany ....... 3210919

[51] Int. Cl.³ ............................................... A61B 17/22
[52] U.S. Cl. .................................... 128/328; 128/24 A
[58] Field of Search ............................. 128/328, 24 A

[56] References Cited

U.S. PATENT DOCUMENTS

| 2,559,227 | 7/1951 | Rieber | 128/24 A |
|---|---|---|---|
| 3,237,623 | 3/1966 | Gordon | 128/24 A |
| 3,251,219 | 5/1966 | Hertz et al. | 128/24 A |
| 3,942,531 | 3/1976 | Hoff et al. | 128/328 |
| 4,216,766 | 8/1980 | Duykers et al. | 128/24 A |
| 4,311,147 | 1/1982 | Häusler | 128/328 |

Primary Examiner—Stephen C. Pellegrino
Assistant Examiner—Gene B. Kartchner
Attorney, Agent, or Firm—Ralf H. Siegemund

[57] ABSTRACT

An apparatus for comminuting concretions in bodies of living beings with a focusing chamber forming part of an ellipsoid of revolution wherein shock waves can be generated by spark discharge at one of the foci, the body being prone in a tub filled with a liquid, where (a) the focusing chamber is sealed by a high-strength membrane,
(b) the focusing chamber is filled with an extensively degassed liquid,
(c) the liquid is under increased pressure, and
(d) the liquid is made to circulate, the liquid being evacuated at a location of the focusing chamber as high as possible, and a liquid free of gas bubbles being replenished into the focusing chamber.

4 Claims, 2 Drawing Figures

APPARATUS FOR COMMINUTING CONCRETIONS IN BODIES OF LIVING BEINGS

The invention relates to an apparatus for comminuting concretions located in the body of a living being by means of a focusing chamber partly assuming the shape of an ellipsoid of rotation and wherein shock waves are generated by an arc discharge at one of the foci, the body being prone in a waterfilled tub.

An apparatus is known for which the focusing chamber is sealed by an elastic membrane and is filled with a liquid, for instance water (German Offenlegungsschrift No. 2,351,247 corresponding to U.S. Pat. No. 3,942,531). Part of the liquid evaporates as the spark ignites (cavitation). A tensile stress of 10–15 bars during pulse widths in the microsecond range, for instance, will suffice to form bubbles in ordinary tap water. Furthermore, the gases dissolved in the liquid (in water for instance: $N_2$, $O_2$, $CO_2$) will be released as bubbles (pseudocavitation). A small portion of the water is also dissociated electrolytically. The transmitted shock waves lose part of their energy at the boundary surfaces of the bubbles they cross, or the waves are partly refracted, scattered, and defocused at these surfaces, and they do not reach their target. Again, the gas bubbles between the electrodes may introduce irregularities in arc propagation. This cited reference discloses no steps to remedy these interferences.

It is an object of the present invention to provide an apparatus for comminuting concretions in bodies of living beings wherein the shock waves arrive at the concretion with the least possible losses.

The advantages of the invention are the following:
- high efficiency because there are few losses in vapor or gas bubbles,
- residual gas bubbles and electrode burn-off are eliminated from the focusing chamber by the exchange of liquids,
- vapor and gas bubbles generated in the spark gaps are quickly dissolved by increased pressure, and accordingly the discharge rate at the spark gap can be increased, and
- because a strong membrane provides reliable separation, liquids which must not contact the body also can be used.

The combination of the three features, no gases, increased pressure, and flows complementing each other in their effects, is very advantageous. Therefore no excessive requirements need be placed on any one of the three features. Thus there is no need for especially intensive degassing of the liquid or keeping it highly degassed, nor is it necessary to circulate the liquid very rapidly or to highly pressurize it. Depending upon need, one of the features may be emphasized, with less intensity placed on the others. In the extreme case, gaseous tap water under extreme high pressure can be used, or no increased pressure is necessary for an extremely gas-free water.

Further advantages, features and applications are discussed in relation to the accompanying drawings, in which:

The two FIGS., 1 and 2, show two embodiments of the invention.

FIG. 1 shows one embodiment of the invention. The figure is a cross-section of a human body 2 with a concretion 4 therein, for instance a kidney stone. To couple-in the shock waves without injury to the body, the body 2 is placed in a tub 8 filled with a coupling liquid 6, for instance water. The body 2 is so positioned with respect to an ellipsoidal focusing chamber 10, provided with a spark gap 12 at one of the foci, that the concretion 4 will be located at the second focus. The positioning means is not shown in the drawing. The focusing chamber 10 is sealed from the water bath 6 by a solid membrane 14 and connected to a liquid circuit containing the liquid 11. This circuit contains a circulating pump 16, the feed 18, the drain 20, a reservoir and compensation vessel 22 with a filter 24 and a liquid-pressurizing means symbolized by the piston 26. A flange 31 to connect to a vacuum degassing device (not shown) is provided at the compensating vessel 22. A system permitting rapid replacement of the spark gap 12 without significant loss of liquid may be additionally provided. Such a system consists in this instance of a cylinder 27, two sliders 25, 29, a bypass line 28, and a valve 30.

Vapor and gas bubbles are generated when the spark gap 12 is ignited, but they immediately dissolve again for the most part. Residual gas bubbles are rinsed away from the spark gap by the circulating liquid and, together with the flow of liquid, pass through the drain 20 and enter the reservoir vessel 22. The flow of liquid also removes bubbles rising at the membrane and adhering thereto. They can dissolve in the reservoir 22, while fresh liquid free of bubbles enters the spark gap 12. If the discharge 20 consists of several apertures 32 surrounding the entire periphery of the membrane, then the low-frequency pressure pulse following each shock wave will assist in expelling the gas bubbles from the focusing chamber 10.

Because the liquid circulating in the focusing chamber 10 is separated in a constant manner from the coupling liquid 6 washing around the body 2, it is possible to use also body-incompatible liquids in the focusing chamber 10. The most important selection criterion is a low vapor pressure of the liquid 11 in the focusing chamber 10. Untreated tap water can be used as the body-incompatible liquid 6 because the energy densities in the tub are sufficiently low that no cavitation takes place.

At substantial time intervals, degassing of the liquid 11 can be effected by connecting a vacuum degassing means to the flange 31.

Another embodiment (not shown) is provided with a focusing chamber with only one discharge opening in the vicinity of the membrane. In this design the focusing chamber is tilted, whereby all the rising gas bubbles arrive at the opening at the highest point of the tub, where they are removed. In this embodiment also, the liquid sweeps over the membrane and removes the bubbles adhering thereto.

Figure 2:
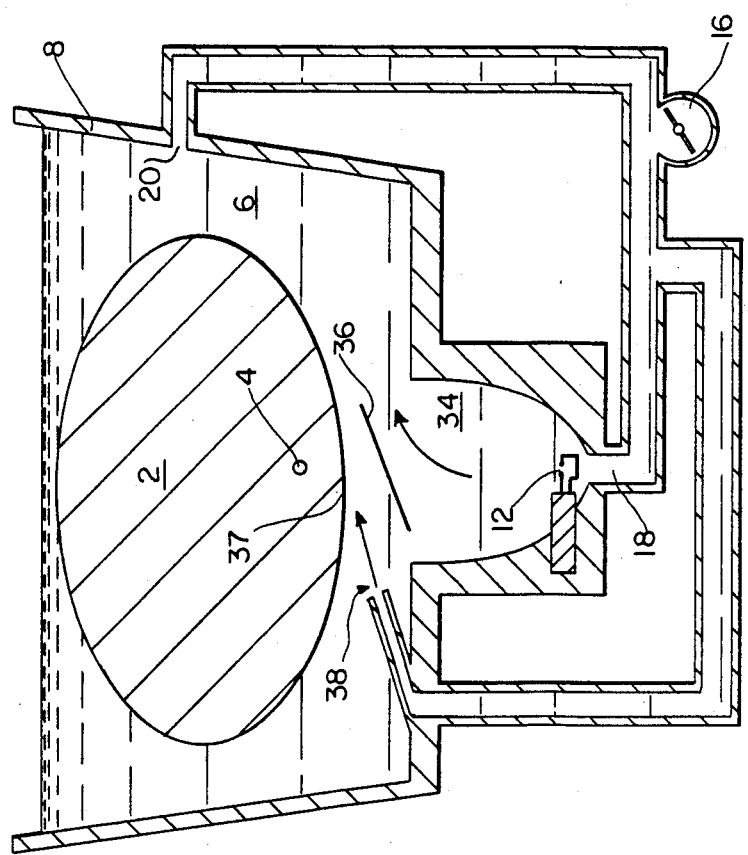

FIG. 2 shows a further embodiment of the invention when lesser intensity shock waves are used; this embodiment operates without increased pressure. Therefore, a sealing membrane is not needed. A slanting, thin foil 36 is mounted between the focusing chamber 34 and the body 2. The focusing chamber 34 is open and the tub 8 and the focusing chamber 34 are washed by the same liquid 6, for instance slightly degassed water. A more intense circulation is provided to compensate for the lack of increased pressure. The flow goes from below, feed 18, through the focusing chamber 34 along the foil 36 (arrow), where it entrains any gas bubbles on that surface. The flow from a second liquid discharge 38 (arrow) prevents gas bubbles flowing into the coupling-in area because of the eddies formed at the foil 36, and removes gas bubbles and contaminations resulting from the physician treating the particular body part 37. The discharge 20 is located in the upper half of the tub 8. The flow in this case also is maintained by a pump 16.

It will be obvious to those skilled in the art that many modifications may be made within the scope of the present invention without departing from the spirit thereof, and the invention includes all such modifications.

What we claim is:

1. In an apparatus for comminuting concretions in the body of a living being and including a focusing chamber forming part of an ellipsoid of revolution having two foci accordingly, further including spark discharge means situated in one of the foci, and the improvement of suppressing the dispersion effect of any gas bubbles comprising:
   a tub for positioning the body so that the concrement becomes situated in a second one of the foci, the focusing chamber being directly mounted to the tub, the tub and the chamber being filled with liquid;
   a common liquid circulation means for flushing liquid through the focusing chamber and the tub and having an inlet for liquid connected to the focusing chamber in the vicinity of the spark discharge means and having an outlet from the tub above the focusing chamber; and
   inclined foil means in the tub under the space provided for the body and mounted above the focusing chamber, said liquid as circulated flowing along one or both of a coupling in location at the body and the lower side of said foil means towards said outlet.

2. In an apparatus for comminuting concretions in the body of a living being and including a focusing chamber forming part of an ellipsoid of revolution having two foci accordingly, further including spark discharge means situated in one of the foci, the body being placed in a tub filled with liquid, the improvement of eliminating shock wave dispersion by bubbles comprising:
   a high strength membrane for sealing the focusing chamber from the tub, the tub being connected to the focusing chamber;
   means for feeding said focusing chamber with an extensively degassed liquid;
   means included in the means for feeding for increasing the pressure of the liquid in the focusing chamber; and
   means for circulating the liquid, including means for extracting the liquid at a high position from the focusing chamber, above the spark generating means, and returning the liquid free from gas bubbles into the focusing by operation of the means for feeding.

3. Apparatus according to claim 2, in which the circulation means comprises a pump (16), a filter (24), a compensating vessel (22), means for pressurization (26), a feed (18) in the vicinity of a spark gap (12) and the means for extracting including a drain (20) with several openings (32) near the membrane.

4. Apparatus according to claim 2, including a system permitting exchanging a spark gap (12) without significant loss of liquid, said system comprising a by-pass line (28), a valve (30), and sliders (25, 29).

* * * * *